US010463764B2

(12) United States Patent
Azab et al.

(10) Patent No.: US 10,463,764 B2
(45) Date of Patent: Nov. 5, 2019

(54) 3D TISSUE-ENGINEERED BONE MARROW FOR PERSONALIZED THERAPY AND DRUG DEVELOPMENT

(71) Applicant: Washington University, St. Louis, MO (US)

(72) Inventors: Abdel Kareem Azab, St. Louis, MO (US); Pilar de la Puente, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 58 days.

(21) Appl. No.: 15/585,653

(22) Filed: May 3, 2017

(65) Prior Publication Data
US 2017/0232146 A1    Aug. 17, 2017

Related U.S. Application Data

(62) Division of application No. 14/942,543, filed on Nov. 16, 2015, now Pat. No. 9,675,732.

(Continued)

(51) Int. Cl.
*C12N 5/074* (2010.01)
*C12N 5/0775* (2010.01)
(Continued)

(52) U.S. Cl.
CPC ......... *A61L 27/3834* (2013.01); *A61L 27/225* (2013.01); *A61L 27/3608* (2013.01); *A61L 27/3804* (2013.01); *A61L 27/3808* (2013.01); *A61L 27/3847* (2013.01); *A61L 27/54* (2013.01); *C12N 5/0669* (2013.01);
(Continued)

(58) Field of Classification Search
CPC ............. A61L 27/3834; A61L 27/3847; A61L 27/3804; A61L 27/3808; A61L 27/54; A61L 27/225; A61L 2430/02; C12N 5/0669; C12N 5/0694; C12N 2533/56; C12N 2513/00
See application file for complete search history.

(56) References Cited

U.S. PATENT DOCUMENTS 5,785,964 A     7/1998   Naughton et al.
2012/0039855 A1  2/2012   Atlas et al.

OTHER PUBLICATIONS

Bensaïd et al., A biodegradable fibrin scaffold for mesenchymal stem cell transplantation. Biomaterials, vol. 24, No. 14 (Jun. 2003) pp. 2497-2502. (Year: 2003).*

(Continued)

*Primary Examiner* — Kara D Johnson
(74) *Attorney, Agent, or Firm* — Polsinelli PC

(57) ABSTRACT

A tissue-engineered bone marrow for personalized therapy of a patient is described. The tissue-engineered bone marrow includes an autologous fibrin scaffold and a plurality of patient-derived cells isolated from the patient's bone marrow. The autologous fibrin scaffold is made using fibrinogen isolated from the patient's bone marrow. The plurality of patient-derived cells may include cells associated with a hematological or metastatic malignancy, bone marrow stromal cells, and endothelial cells. The patient-derived cells are cultured on the autologous fibrin scaffold to create the tissue-engineered bone marrow. The tissue-engineered bone marrow may be used for personalized drug screening.

12 Claims, 7 Drawing Sheets
(7 of 7 Drawing Sheet(s) Filed in Color)

Related U.S. Application Data

(60) Provisional application No. 62/079,868, filed on Nov. 14, 2014.

(51) Int. Cl.
*A61L 27/38* (2006.01)
*A61L 27/22* (2006.01)
*G01N 33/50* (2006.01)
*C12N 5/077* (2010.01)
*C12N 5/09* (2010.01)
*A61L 27/54* (2006.01)
*A61L 27/36* (2006.01)

(52) U.S. Cl.
CPC ....... *C12N 5/0694* (2013.01); *G01N 33/5011* (2013.01); *G01N 33/5082* (2013.01); *G01N 33/5088* (2013.01); *A61L 2300/414* (2013.01); *A61L 2300/418* (2013.01); *A61L 2300/42* (2013.01); *A61L 2300/426* (2013.01); *A61L 2300/64* (2013.01); *A61L 2430/02* (2013.01); *A61L 2430/40* (2013.01); *C12N 2502/30* (2013.01); *C12N 2513/00* (2013.01); *C12N 2533/56* (2013.01)

(56) References Cited

OTHER PUBLICATIONS

De la Puente et al., Cell culture in autologous fibrin scaffolds for applications in tissue engineering. Experimental Cell Research, vol. 322, No. 1 (Mar. 2014) pp. 1-11. (Year: 2014).*

Bensaid, W. et al., "A biodegradable fibrin scaffold for mesenchymal stem cell transplantation," Biomaterials, 2003, pp. 2497-2502, vol. 24, Elsevier Science Ltd.

De La Puente, P. et al., "Differentiation within autologous fibrin scaffolds of porcine dermal cells with the mesenchymal stem cell phenotype," Exp. Cell Res., 2013, pp. 144-152, vol. 319, Elsevier Inc.

De La Puente, P. et al., "Autologous fibrin scaffolds cultured dermal fibroblasts and enriched with encapsulated bFGF for tissue engineering," J. Biomed. Mater. Res., Part A, 2011, pp. 648-654, vol. 99A, Wiley Periodicals, Inc.

De La Puente, P. et al., "Cell culture in autologous fibrin scaffolds for applications in tissue engineering," Exp. Cell Res., 2014, pp. 1-11, vol. 322, Elsevier Inc.

Ferrarini, M. et al., "Ex-Vivo Dynamic 3-D Culture of Human Tissues in the RCCS™' Bioreactor Allows the Study of Multiple Myeloma Biology and Response to Therapy," PLoS One, Aug. 26, 2013, pp. 1-10, vol. 8, No. 8, e71613.

* cited by examiner

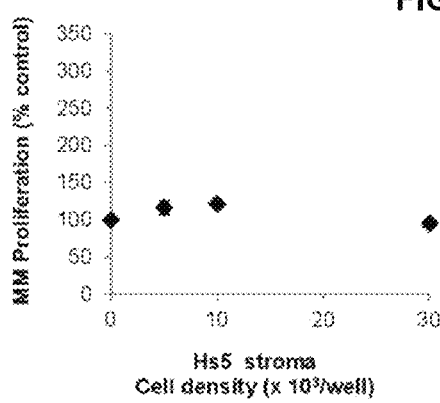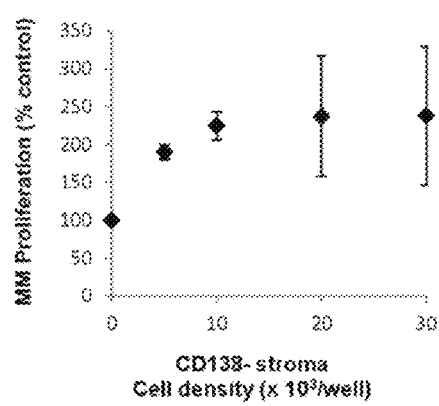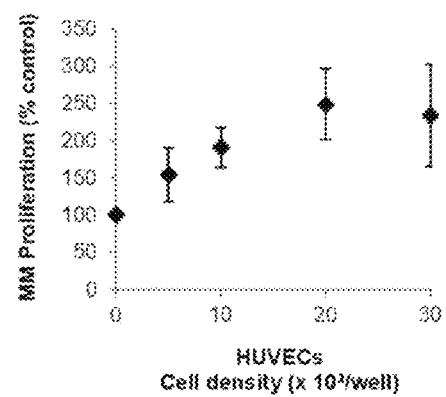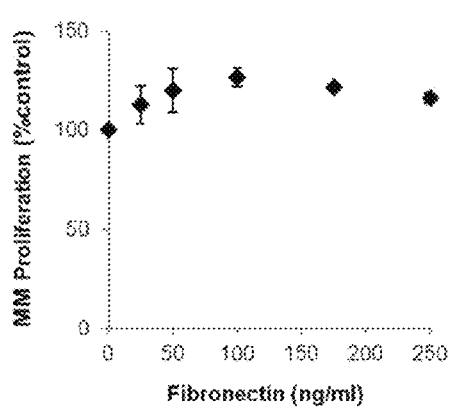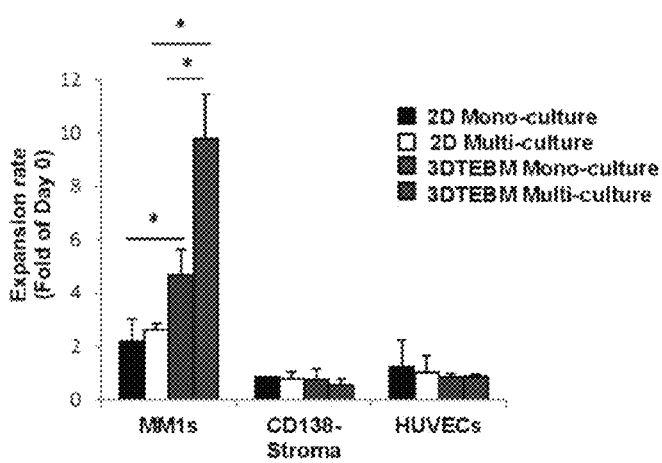

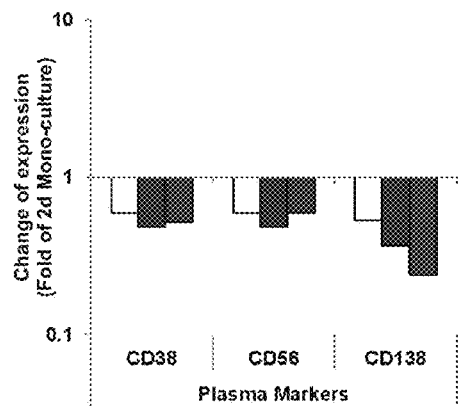
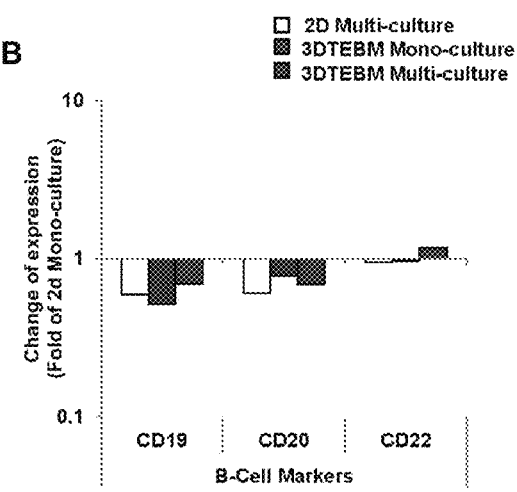
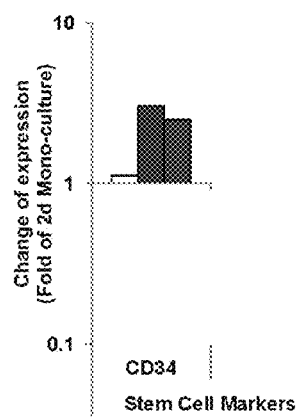

3D TISSUE-ENGINEERED BONE MARROW FOR PERSONALIZED THERAPY AND DRUG DEVELOPMENT

CROSS REFERENCE TO RELATED APPLICATIONS

This application is a divisional application of U.S. application Ser. No. 14/942,543 filed on Nov. 16, 2015, which claims priority from U.S. provisional patent application Ser. No. 62/079,868 entitled "3D Tissue Engineered Bone Marrow for Personalized Therapy and Drug Development" filed on Nov. 14, 2014, both of which are hereby incorporated by reference herein in their entirety.

FIELD OF THE INVENTION

This application relates to a tissue-engineered bone marrow and methods of preparing and using the tissue-engineered bone marrow for personalized therapy of a patient. In particular, this application relates to a tissue-engineered bone marrow including an autologous fibrin scaffold with fibrinogen isolated from the patient's bone marrow and a plurality of patient-derived cells isolated from the patient's bone marrow, such as, cells associated with a hematological or metastatic malignancy, bone marrow stromal cells, and endothelial cells.

BACKGROUND OF THE INVENTION

Multiple myeloma (MM) is the second most prevalent hematological malignancy and remains incurable with a median survival of three to five years. Despite the introduction of several novel drugs and the high efficacy of these drugs shown in vitro, less than 60% of patients respond to therapy upfront, and more than 90% relapse and develop drug resistance. The discrepancy between in vitro efficacy and clinical outcomes can be attributed to several limitations of the classic tissue culture drug screening models including: (1) Most of the in vitro models use MM cell line cultures and neglect the vital role of the bone marrow (BM) microenvironment in MM progression, which promotes drug resistance; (2) The BM niche is a three-dimensional (3D) structure with a gradient of both oxygen and drug concentration as a function of distance from blood vessels. The vascular niche (close to the blood vessels) presents high oxygenation levels, includes more proliferative cells, and receives higher drug concentrations, while the endosteal niche (close to the bone) is hypoxic, receives lower drug concentrations, and includes less proliferative but more drug-resistant cells. The classic two-dimensional (2D) in vitro tissue culture system cannot mimic oxygen and drug gradients in culture wells, making all cells highly oxygenated; therefore, 2D cultures cannot accurately predict drug sensitivity in different parts of the BM niche due to lack of accurate effects throughout various tissue depths; and (3) The MM patient population is highly variable, both genetically and epigenetically, and the biological characteristics of patients are widely different, which demonstrates sensitivity of individual patients to different therapies. Typical 2D models rely on a limited number of MM cell lines which cannot reflect the enormous heterogeneity and variations present in individual patients.

Several 3D MM models were developed based on Matrigel scaffolds, acrylic polymers, and human bone chips. These provide a better alternative compared to 2D cultures; however, each has its limitations. The Matrigel and synthetic polymer-based models are made from materials which are not physiologically found in the BM and may cause significant changes in interactions between different culture components and the matrix. The bone-chip-based model is closer to BM physiological conditions; however, it is technically challenging, as it needs about eight weeks before it is ready for drug testing. Also, it relies on interaction of MM cells with a normal BM microenvironment, which was proven to be significantly different from the MM microenvironment. All together, these three models are based on foreign materials and refer to all MM patients as one group, ignoring inherent heterogeneity. Therefore, a need exists to develop a better model for testing drug efficacy that takes into account these factors.

SUMMARY OF INVENTION

In an aspect, a tissue-engineered bone marrow for personalized therapy of a patient is provided that may include an autologous fibrin scaffold, and a plurality of patient-derived cells isolated from the patient's bone marrow. The autologous fibrin scaffold may include fibrinogen isolated from the patient's bone marrow. The patient-derived cells may include cells associated with a hematological or metastatic malignancy, bone marrow stromal cells, and endothelial cells. The patient-derived cells may be cultured on the autologous fibrin scaffold. The autologous fibrin scaffold may further include a cross-linking agent that may include calcium chloride and an antifibrinolytic agent that may include tranexamic acid. The autologous fibrin scaffold may further include patient-derived culture compounds extracted from the patient's bone marrow. The patient-derived culture compounds may include: fibronectin, at least one growth factor, platelets, at least one cytokine, and at least one enzyme. The tissue-engineered bone marrow may further include a drug. The autologous fibrin scaffold may further include a gradient of oxygen and the drug. The cells associated with a hematological or metastatic malignancy may be selected from acute lymphoblastic leukemia cells, acute myelogenous leukemia cells, chronic lymphocytic leukemia cells, acute monocytic leukemia cells, Hodgkin's lymphoma cells, non-Hodgkin's lymphoma cells, multiple myeloma cells, metastatic cells, and solid tumor cells. The cells associated with a hematological or metastatic malignancy may be multiple myeloma cells. The multiple myeloma cells may be de-differentiated.

In another aspect, a method of preparing a tissue-engineered bone marrow for personalized therapy of a patient is provided that may include aspirating the patient's bone marrow, separating a cellular fraction and a supernatant, isolating a plurality of patient-derived cells from the cellular fraction, creating an autologous fibrin scaffold, and culturing the plurality of patient-derived cells on the fibrin scaffold. The patient-derived cells may include cells associated with a hematological or metastatic malignancy, bone marrow stromal cells and endothelial cells. The autologous fibrin scaffold may include fibrinogen isolated from the supernatant. The autologous fibrin scaffold may further include a cross-linking agent that may include calcium chloride and an antifibrinolytic agent that may include tranexamic acid. The autologous fibrin scaffold may further include fibronectin, growth factors, platelets, cytokines, and enzymes isolated from the supernatant. The method may further include administering a dose of a drug to the tissue-engineered bone marrow. The autologous fibrin scaffold may further include a gradient of oxygen and the drug. The cells associated with a hematological or metastatic malignancy may be selected from acute lymphoblastic leukemia cells, acute myelogenous leukemia cells, chronic lymphocytic leukemia cells, acute monocytic leukemia cells, Hodgkin's lymphoma cells, non-Hodgkin's lymphoma cells, multiple myeloma cells, metastatic cells, and solid tumor cells. The cells associated with a hematological or metastatic malignancy may be multiple myeloma cells. The multiple myeloma cells may be de-differentiated.

In an additional aspect, a method of drug screening using a prepared tissue-engineered bone marrow for personalized therapy of a patient is provided. The method may include applying a drug at a dose to the tissue-engineered bone marrow and predicting the drug response in the patient based on the effectiveness of the drug and the dose in the tissue-engineered bone marrow. The tissue-engineered bone marrow may include: an autologous fibrin scaffold and a plurality of patient-derived cells isolated from the patient's bone marrow. The patient-derived cells may be cultured on the autologous fibrin scaffold. The autologous fibrin scaffold may include fibrinogen isolated from the patient's bone marrow. The patient-derived cells may include: cells associated with a hematological or metastatic malignancy, bone marrow stromal cells, and endothelial cells. The autologous fibrin scaffold may further include a cross-linking agent including calcium chloride and an antifibrinolytic agent including tranexamic acid. The autologous fibrin scaffold may further include patient-derived culture compounds extracted from the patient's bone marrow. The patient-derived culture compounds may include: fibronectin, at least one growth factor, platelets, at least one cytokine, and at least one enzyme. The method may further include administering a dose of a drug to the tissue-engineered bone marrow. The autologous fibrin scaffold may further include a gradient of oxygen and the drug. The cells associated with a hematological or metastatic malignancy may be selected from acute lymphoblastic leukemia cells, acute myelogenous leukemia cells, chronic lymphocytic leukemia cells, acute monocytic leukemia cells, Hodgkin's lymphoma cells, non-Hodgkin's lymphoma cells, multiple myeloma cells, metastatic cells, and solid tumor cells. The cells associated with a hematological or metastatic malignancy may be multiple myeloma cells. The multiple myeloma cells may be de-differentiated. The effectiveness of the drug and the dose may be determined by drug uptake by the plurality of cells or cell death of the multiple myeloma cells. Predicting the drug response in the patient may include determining patient-specific drug resistance. The patient may have a disease selected from the group consisting of hematologic malignancies, multiple myeloma, and bone metastasis of solid tumors.

In another additional aspect, a tissue-engineered scaffold is provided that includes: an autologous fibrin scaffold that includes: fibrinogen isolated from a bone marrow of a patient; and a plurality of patient-derived cells isolated from the bone marrow of the patient. The patient-derived cells may stem cells and endothelial cells. The patient-derived cells may be cultured on the fibrin scaffold. The plurality of patient-derived cells may further include endothelial cells.

The patient-derived 3D tissue-engineered bone marrow for personalized therapy and drug development, may provide a tool to predict better drug responses in patients and develop a personalized therapeutic strategy for every single patient based on the biological variants and characteristics of the patients own disease. The model may provide for in vitro personalized drug screening, prediction of therapeutic efficacy, and prediction of relapse, for the treatment of MM, or any other malignancy. The model may identify the right treatment for each patient, based on this new tool for drug development screening. The model may provide a better in vitro model than classic 2D cultures for drug development and drug discovery by incorporating elements to mimic the biological characteristics of tumor microenvironment for better prediction of the effect in vivo. This same concept can be further extended to other diseases, since the BM-microenvironment is known to play a crucial role in other hematologic malignancies such as leukemia and lymphoma.

BRIEF DESCRIPTION OF THE DRAWINGS

The application file contains at least one photograph executed in color. Copies of this patent application publication with color photographs will be provided by the Office upon request and payment of the necessary fee.

FIG. 3A shows the effect of co-culture of MM cells ($30 \times 10^3$ cells/well) with Hs5 stroma cells ($0 \times 10^3$-$30 \times 10^3$ cells/well) on the growth of MM1s cells inside 3DTEBM at day 3.

FIG. 3B shows the effect of co-culture of MM cells ($30 \times 10^3$ cells/well) with CD138$^-$ stroma cells ($0 \times 10^3$-$30 \times 10^3$ cells/well) on the growth of MM1s cells inside 3DTEBM at day 3.

FIG. 3C shows the effect of co-culture of MM cells ($30 \times 10^3$ cells/well) with HUVECs ($0 \times 10^3$-$30 \times 10^3$ cells/well) on the growth of MM1s cells inside 3DTEBM at day 3.

FIG. 3D shows the effect of incorporation of fibronectin (0-250 mg/ml) on the growth of MM1s cells inside 3DTEBM at day 3.

FIG. 3E shows growth of MM1s cells, CD138$^-$ stroma cells, and HUVECs in mono-culture or multi-culture conditions in classic 2D cultures or inside 3DTEBM at day 3, (*) $p < 0.02$.

FIG. 6A shows the effect of classic 2D cultures and 3DTEBM, in mono- or multi-culture conditions, on the expression of plasma markers including CD38, CD56, and CD138 after 3 days.

FIG. 6B shows the effect of classic 2D cultures and 3DTEBM, in mono- or multi-culture conditions, on the expression of B cell markers including CD19, CD20, and CD22 after 3 days.

FIG. 6C shows the effect of classic 2D cultures and 3DTEBM, in mono- or multi-culture conditions, on the expression of the stem cell marker CD34 after 3 days.

Corresponding reference characters indicate corresponding elements among the views of the drawings. The headings used in the figures should not be interpreted to limit the scope of the claims.

DETAILED DESCRIPTION

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities and plural terms shall include the singular.

The use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Figure 1A:
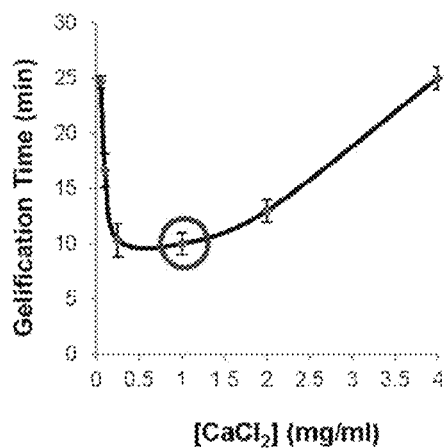
FIG. 1A shows the effect of calcium chloride concentration (0-4 mg/ml) on the gelification time of 3DTEBM. Note in a circle the calcium chloride concentration (1 mg/ml) which induced the fastest gelification time.
Figure 1B:
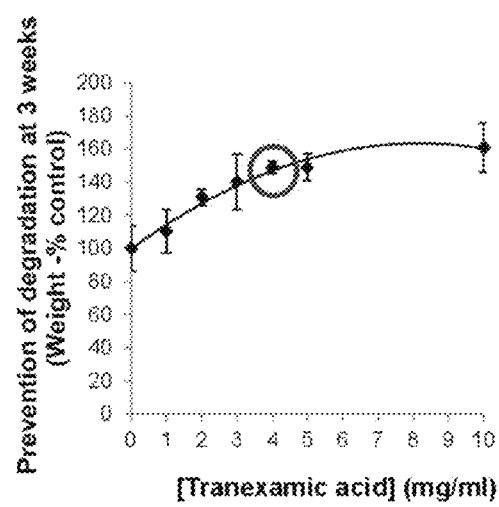
FIG. 1B shows the effect of tranexamic acid concentration (0-10 mg/ml) on the stability of 3DTEBM. Note in a circle the tranexamic acid concentration (4 mg/ml) which induced maximal 3DTEBM stabilization.
Figure 1C:
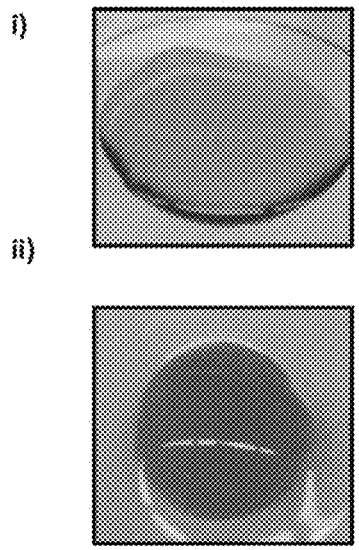
FIG. 1C shows visual images of (i) non-cross-linked BM supernatant with media and (ii) cross-linked 3DTEBM.
Figure 1D:
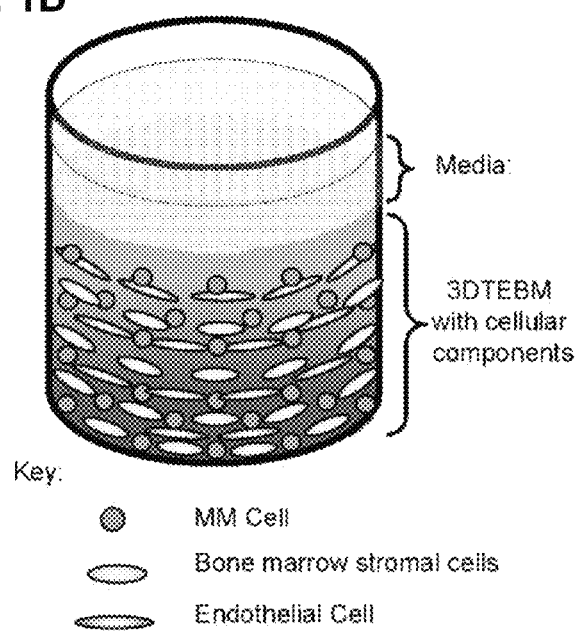
FIG. 1D shows design of a 3DTEBM in a well of a 96-well plate showing crosslinked scaffold with homogeneous dispersion of cellular components (MM, BMSCs, and ECs) and media on top.
Figure 7:
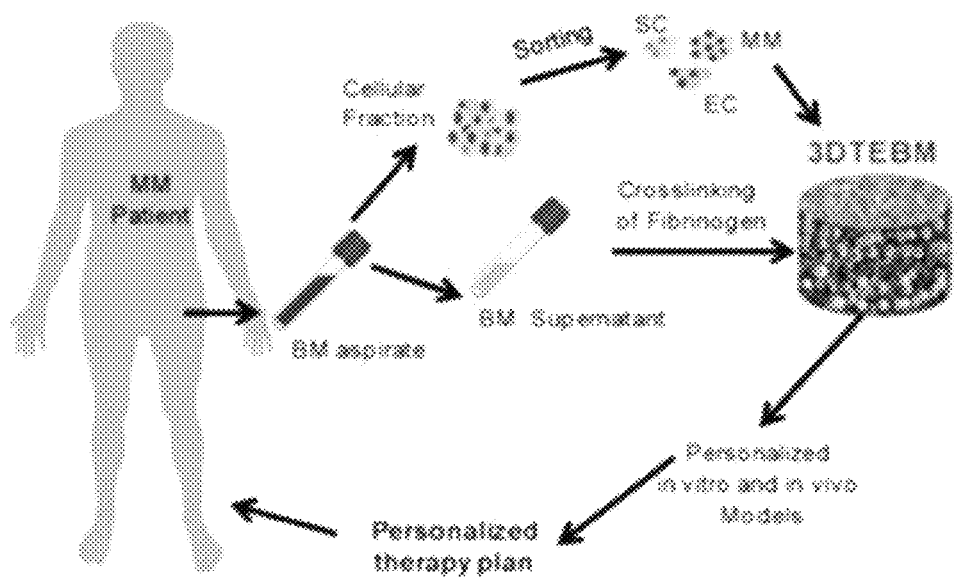
FIG. 7 illustrates the development of a personalized therapeutic plan based on a personalized 3DTEBM.

The present disclosure encompasses compositions and methods for using 3D tissue-engineered bone marrow (3DTEBM) as a model for the study of multiple myeloma (MM) biology, for in vitro examination of tumor microenvironment and interactions between myeloma cells and accessory cells, and a patient-derived reproducible, inexpensive and readily available model for support of primary myeloma ex vivo growth, in vitro examination of antimyeloma drugs, and for further patient-targeted drug therapy in MM. FIG. 7 illustrates the development of a personalized therapeutic plan based on a personalized 3DTEBM. The 3DTEBM may be manufactured by cross-linking of bone marrow (BM) supernatants and cells from the same multiple myeloma patient, which makes it the closest possible model to the BM of specific patients and provides better prediction of therapeutic responses. The 3DTEBM may be generated by cross-linking BM supernatant (including endogenous soluble growth factors and cytokines) and by incorporating mononuclear cells (including MM and accessory cells) from the same patients (FIG. 1D).

I. 3D Tissue Engineered Bone Marrow

Fibrin-based scaffolds are biocompatible and biodegradable, and provide stability for grafted cells. In blood coagulation, fibrin forms a protein mesh that result from the polymerization of fibrinogen. Calcium ions facilitate the conversion of fibrinogen molecules to fibrin. The interaction of calcium ions with fibrinogen, factor XIIIa and other coagulation proteins may increase bonding strength and decrease the gelling time for 3DTEBM cross-linking.

In an aspect, a tissue-engineered bone marrow for personalized therapy of a patient may include an autologous fibrin scaffold and a plurality of patient-derived cells isolated from the patient's bone marrow. In various aspects, the patient-derived cells may include, but are not limited to, cells associated with a hematological or metastatic malignancy, bone marrow stromal cells, and endothelial cells. In an aspect, a tissue-engineered scaffold may include an autologous fibrin scaffold comprising fibrinogen isolated from a bone marrow of a patient and a plurality of patient-derived cells isolated from the bone marrow of the patient, the patient-derived cells comprising stem cells and endothelial cells. In this aspect, the plurality of patient-derived cells may further include bone marrow stromal cells. The patient-derived cells may be cultured on the autologous fibrin scaffold.

The autologous fibrin scaffold may be made from fibrinogen isolated from the patient's bone marrow. In an aspect, the fibrinogen may be isolated from the patient's plasma. The fibrinogen, in combination with thrombin, may form the autologous fibrin scaffold. The autologous fibrin scaffold may further include a cross-linking agent, for example calcium chloride.

Fibrin-based scaffolds can degrade rapidly. Therefore, use of an antifibrinolytic agent may reduce fibrin degradation and maintain integrity and stability. In an aspect, the autologous fibrin scaffold may further include an antifibrinolytic agent. Use of an antifibrinolytic agent may not affect cell viability. In an aspect, the antifibrinolytic agent may be, but is not limited to tranexamic acid, aminocaproic acid (ε-aminocaproic acid), aprotinin, or a lysine-like drug that interferes with the formation of the fibrinolytic enzyme plasmin. In one aspect, the antifibrinolytic agent may be tranexamic acid.

The autologous fibrin scaffold may further include patient-derived culture compounds extracted from the patient's bone marrow. Non-limiting examples of patient-derived culture compounds include fibronectin, at least one growth factor, platelets, at least one cytokine, at least one enzyme, and combinations thereof. The at least one growth factor may include, but is not limited to erythropoietin (EPO), darbapoietin, G-CSF (granulocyte colony-stimulating factors), or GM-CSF (granulocyte macrophage colony-stimulating factors). Non-limiting examples of the at least one cytokine include SCF, GM-CSF, G-CSF, TGF-beta, IL-6, IL-7, IL-8, and IL-11. The at least one enzyme may include, but is not limited to lactic dehydrogenase (LDH), glutamic-oxalacetic transaminase (GOT), and acid and alkaline phosphatase.

The cells associated with a hematological or metastatic malignancy may include, but are not limited to, acute lymphoblastic leukemia cells, acute myelogenous leukemia cells, chronic lymphocytic leukemia cells, acute monocytic leukemia cells, Hodgkin's lymphoma cells, non-Hodgkin's lymphoma cells, multiple myeloma cells, metastatic cells, and solid tumor cells. In one aspect, the cells associated with a hematological or metastatic malignancy may be multiple myeloma cells. The multiple myeloma cells may be de-differentiated.

Figure 2A:
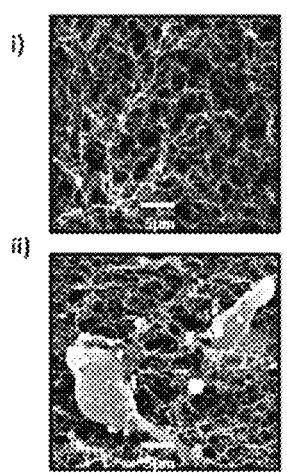
FIG. 2A is electron microscopy images of 3DTEBM i) without and ii) with MM cells. Scale bar=5 µm.
Figure 2B:
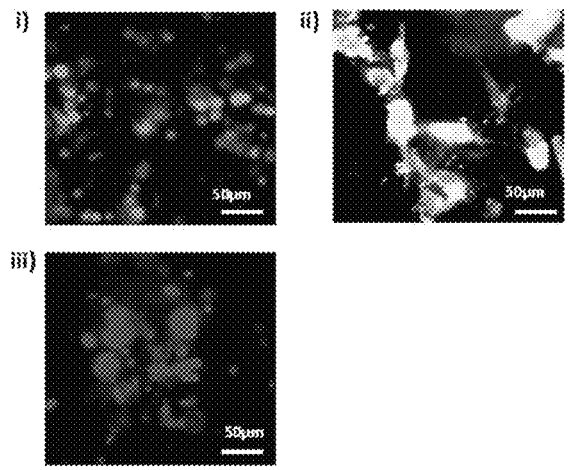
FIG. 2B is fluorescence microscopy images of i) MM1s-GFP, ii) HUVECs-DiI, and iii) CD138$^-$ stroma-DiD growing inside 3DTEBM at day 3. Scale bar=50 µm.

In various aspects, the 3DTEBM creates a BM microenvironment to facilitate MM cell growth. The 3D structure of 3DTEBM comprises a network of interconnecting pores, through which cells migrate, multiply and spread along the scaffold (FIG. 2A and FIG. 2B). MM1s, stromal cells, and HUVECs may interact with the fibers of the fibrin scaffold. The MM1s cells may proliferate in the 3DTEBM. In one aspect, the MM1s may show a 4.5 fold increase in the expansion rate compared to a 1-2 fold increase for the other cells. 3DTEBM may selectively stimulate MM1s proliferation, and this effect may be enhanced by recreating BM interactions with a multi-culture strategy. Co-culture of MM1s with normal stroma (Hs5 cell line) may increase MM proliferation. However, malignant CD138– stroma cells from MM patients or HUVECs may considerably increase the growth of MM in the 3DTEBM. Without being limited to a particular theory, MM bone marrow stem cells (BMSCs) may support MM growth by derived exosomes with higher levels of oncogenic proteins, cytokines, and adhesion molecules compared with exosomes from normal cells. In addition, fibronectin may be incorporated into the 3DTEBM to increase MM proliferation. VLA4 expressed on multiple myeloma cells mediates binding to the extracellular matrix (ECM), through fibronectin, which confers cell-adhesion-mediated drug resistance. When mono-culture and multi-culture conditions in the classic 2D cultures and 3DTEBM were compared, the 3DTEBM was found to be able to host MM cell growth better than classic systems, and the multi-culture conditions (accessory cells and ECM components), which recreates the BM interactions of the BM microenvironment, enhanced even more MM growth.

Current methods to assess MM cancer treatments are often inaccurate, in part, due to limitations in the classic laboratory models which fail to recreate the BM microenvironment. The interaction of MM cells with ECM and accessory cells in the BM play a crucial role in MM progression and drug resistance. The BM niche presents gradient of both oxygen and drug concentration as a function of distance from blood vessels. The vascular niche (close to the blood vessels) presents high oxygenation levels, includes more proliferative cells, and receives higher drug concentrations, while the endosteal niche (close to the bone) is hypoxic, receives lower drug concentrations, and includes less proliferative but more drug-resistant cells. In the vascular niche, angiogenic factors and cytokines activate an angiogenic switch that promotes tumor growth. In contrast, the endosteal niche maintains quiescence and prevents differentiation of attached haematopoietic stem cells.

The tissue-engineered bone marrow may further include a drug. In an aspect, the drug may be a chemotherapeutic drug. Non-limiting examples of drugs include melphalan, bortezomib, carfilzomib, carmustine, cyclophosphamide, doxorubicin hydrochloride liposome, lenalidomide, pamidronate disodium, panobinostat, plerixafor, pomalidomide, prednisone, thalidomide, zoledronic acid, and any drug being tested for treatment of multiple myeloma. In an aspect, the autologous fibrin scaffold may further include a gradient of oxygen and the drug. In this aspect, the autologous fibrin scaffold may mimic the BM niche. The concentration of oxygen may decrease as a function of depth in the autologous fibrin scaffold. Furthermore, hypoxia in the patient-derived cells cultured on the autologous scaffold may increase as a function of depth in the autologous fibrin scaffold.

MM cells cultured in 3DTEBM may have a higher hypoxic state and lower doxorubicin drug uptake compared to cells cultured in 2D models, because BM of MM patients was shown to be hypoxic and have a slower diffusion of drugs in a 3D model. Tumor growth in MM may induce hypoxic conditions in the BM, a concept that has also been confirmed in other hematologic malignancies. Several studies have indicated that the hypoxic microenvironment contributes to cancer progression and hypoxia was also related to induce drug resistance. The 3DTEBM recreates drug gradients as a function of the depth of the tissue, such as the ones in the BM niche. This may explain the reduced-activity of drugs in a three-dimensional environment. Therefore, a patient-derived three-dimensional tissue-engineered bone marrow (3DTEBM) may be able to recreate BM interactions, and hypoxia and drug gradients by reproducing tissue-specific structural features and cell-cell interactions more accurately than conventional 2D cultures. Moreover, the model may recapitulate more closely physical features of the BM, such as the endosteal and vascular niche.

Furthermore, the 3DTEBM may induce loss of plasma cell markers and over-expression of stem cell markers. The 3DTEBM cultures may induce dedifferentiation of MM cells, and a stem-cell-like phenotype might be developing. Without being limited to a particular theory, de-differentiation may be a key mechanism for the generation of tumor-initiating cells in human cancer, and this process may be under the control of tumor microenvironment. Stem-cell-like MM cells are thought to be the subpopulation which remains after treatment and promote relapse in patients. 3DTEBM may have an effect on the plenotypic changes of tumor cells. The cancer stem cells (CSC) phenotype is a plastic state induced in cancer cells by microenvironmental signals, including hypoxia. Therefore, the 3DTEBM might be able to recreate the BM microenvironment signals by inducing cell de-differentiation and drug resistance. The 3DTEBM may be an in vitro tool for studying the tumor microenvironment and analyzing the number of the stem cell-like MM cells remaining after drug treatment. The 3DTEBM, especially in the presence of accessory cells, may induce stem cell-like properties in the MM cells, and that the drug treatments may kill the cells which are not stem cell-like, and therefore enrich for cells which are more resistant and stem cell-like, that will remain in the 3DTEBM and mimic micro-residual disease.

The 3DTEBM may promote primary myeloma ex vivo growth compared to classic 2D models. In vitro culturing of primary myeloma cells has been a major challenge because the lack of an in vitro technology capable of recreating the complicated bone marrow microenvironment which MM cells depend on for its survival. While primary myeloma cells cannot grow ex vivo in SCID mice, they are able to growth in SCIDhu mice. However, animal models are expensive, time-consuming, and often have limited reproducibility. In addition, classic laboratory models cannot take into consideration the variability of disease in every patient, and the MM patient population is highly variable, both genetically and epigenetically, and the biological characteristics of patients are widely different, which demonstrates sensitivity of individual patients to different therapies. Typical 2D models rely on a limited number of MM cell lines which cannot reflect the enormous heterogeneity and variations present in individual patients. The 3DTEMB resolves the limitations of classic laboratory models by cross-linking BM supernatant, including endogenous soluble growth factors and cytokines, and by incorporating mononuclear cells, including MM (CD138$^+$ population) and accessory cells (CD138$^-$ population), from the same patients. It has been shown that MM BMSCs and MM ECs are different compared to normal stromal cells or endothelial cells; therefore, the CD138$^-$ population preservation and maintenance in the model is important.

The 3DTEBM support primary MM growth better than classic systems, and the multi-culture conditions (CD138$^-$ population from the same patient and ECM components), which recreates the personalized BM microenvironment and enhances even more MM growth. The BM microenvironment facilitates primary MM cell growth, previously shown with cell lines. In addition, the 3DTEBM supports primary MM growth of fresh, as well as, frozen patient samples. The 3DTEBM provides versatility, adaptability, and availability as a new tool for personalized primary tumor growth in any moment desired. A 3DTEBM allows long-term culture of primary myeloma cells ex vivo, and the 3DTEBM may be utilized for studying multiple myeloma biology and for testing patient-targeted therapy.

II. Method of Preparing a Tissue-Engineered Bone Marrow

In an aspect, a method of preparing a tissue-engineered bone marrow for personalized therapy of a patient may include aspirating the patient's bone marrow, separating a cellular fraction and a supernatant, isolating a plurality of patient-derived cells from the cellular fraction, creating an autologous fibrin scaffold, and culturing the plurality of patient-derived cells on the fibrin scaffold. Non-limiting examples of the patient-derived cells include cells associated with a hematological or metastatic malignancy, bone marrow stromal cells and endothelial cells.

In an aspect, the autologous fibrin scaffold may be made using fibrinogen isolated from the supernatant. In one aspect, the fibrinogen may be isolated from the patient's plasma. The fibrinogen, in combination with thrombin, may form the autologous fibrin scaffold. The autologous fibrin scaffold may further include a cross-linking agent, for example calcium chloride. The concentration of calcium chloride used to form the fibrin scaffolds may range from about 0 mg/ml to about 5 mg/ml. In a preferred aspect, the calcium chloride concentration may be about 1 mg/ml for fibrin-based scaffolds development.

Use of an antifibrinolytic agent may reduce fibrin degradation, maintain integrity and stability. In an aspect, the method may further include creating the autologous fibrin scaffold with an antifibrinolytic agent. Use of an antifibrinolytic agent may not affect cell viability. In an aspect, the antifibrinolytic agent may be, but is not limited to tranexamic acid, aminocaproic acid (ε-aminocaproic acid), aprotinin, or a lysine-like drug that interferes with the formation of the fibrinolytic enzyme plasmin. In one aspect, the antifibrinolytic agent may be tranexamic acid. In various aspects, a concentration of tranexamic acid used to form the fibrin scaffolds may range from about 0 mg/ml to about 10 mg/ml. In one aspect, a tranexamic acid concentration of 4 mg/ml may maintain stable scaffolds at least for about 3 weeks in culture. In one aspect, a 3DTEBM may be formed by mixing the following components to achieve final concentrations of 400 μl/ml plasma, 1 mg/ml calcium chloride, and 4 mg/ml tranexamic acid diluted in RPMI completed media to form 100 μl scaffolds. In an aspect, the 3DTEBM may be a stable 3D model for at least about 3 weeks. Cells may be added to the mixing solution before fibrin clotting agents (calcium chloride and tranexamic acid).

The autologous fibrin scaffold may further include patient-derived culture compounds isolated from the supernatant. Non-limiting examples of patient-derived culture compounds include fibronectin, at least one growth factor, platelets, at least one cytokine, at least one enzyme, and combinations thereof. In an aspect, fibronectin may be present in the autologous fibrin scaffold in a concentration ranging from about 0 ng/ml to about 1000 ng/ml. In one aspect, the concentration of fibronectin may be about 100 ng/ml. The at least one growth factor may include, but is not limited to erythropoietin (EPO), Darbapoietin, G-CSF (granulocyte colony-stimulating factors), or GM-CSF (granulocyte macrophage colony-stimulating factors). Non-limiting examples of the at least one cytokine include SCF, GM-CSF, G-CSF, TGF-beta, IL-6, IL-7, IL-8, and IL-11. The at least one enzyme may include, but is not limited to lactic dehydrogenase (LDH), glutamic-oxalacetic transaminase (GOT), and acid and alkaline phosphatase.

The cells associated with a hematological or metastatic malignancy may include, but are not limited to, acute lymphoblastic leukemia cells, acute myelogenous leukemia cells, chronic lymphocytic leukemia cells, acute monocytic leukemia cells, Hodgkin's lymphoma cells, non-Hodgkin's lymphoma cells, multiple myeloma cells, metastatic cells, and solid tumor cells. In one aspect, the cells associated with a hematological or metastatic malignancy may be multiple myeloma cells. The multiple myeloma cells may be de-differentiated.

The method may further include administering a dose of a drug to the tissue-engineered bone marrow. In an aspect, the drug may be a chemotherapeutic drug. Non-limiting examples of drugs include melphalan, bortezomib, carfilzomib, carmustine, cyclophosphamide, doxorubicin hydrochloride liposome, lenalidomide, pamidronate disodium, panobinostat, plerixafor, pomalidomide, prednisone, thalidomide, zoledronic acid, and any drug being tested for treatment of multiple myeloma. In an aspect, the autologous fibrin scaffold may further include a gradient of oxygen and the drug. In this aspect, the autologous fibrin scaffold may mimic the BM niche. The concentration of oxygen may decrease as a function of depth in the autologous fibrin scaffold. Furthermore, hypoxia in the patient-derived cells cultured on the autologous scaffold may increase as a function of depth in the autologous fibrin scaffold.

III. Method of Drug Screening

3DTEBM may be used as a drug screening system. IC50 of different chemotherapy drugs commonly used in MM showed the same therapeutic pattern, where 3D system induced stronger resistance and the multi-culture conditions increased the effect even more. The 3DTEBM may induce drug resistance in MM cells, especially when it contains accessory cells and ECM components. Specifically, MM cells express surface adhesion receptor molecules which bind with corresponding ligands on stromal cells or ECM components, responsible for the cell adhesion-mediated drug resistance (CAM-DR). Therefore, the 3DTEBM is able to recreate drug resistance better than 2D models.

In various aspects, the present disclosure provides for a method of drug screening using a prepared tissue-engineered bone marrow for personalized therapy of a patient. In an aspect, the method may include applying a drug at a dose to the tissue-engineered bone marrow, and predicting the drug response in the patient based on the effectiveness of the drug and the dose in the tissue-engineered bone marrow. The tissue-engineered bone marrow may include an autologous fibrin scaffold comprising fibrinogen isolated from the patient's bone marrow and a plurality of patient-derived cells isolated from the patient's bone marrow. In various aspects, the patient-derived cells may include cells associated with a hematological or metastatic malignancy, bone marrow stromal cells, and endothelial cells. The patient-derived cells are cultured on the autologous fibrin scaffold.

The autologous fibrin scaffold may be made from fibrinogen isolated from the patient's bone marrow. In an aspect, the fibrinogen may be isolated from the patient's plasma. The fibrinogen, in combination with thrombin, may form the autologous fibrin scaffold. The autologous fibrin scaffold may further include a cross-linking agent, for example calcium chloride.

Fibrin-based scaffolds can degrade rapidly. Therefore, use of an antifibrinolytic agent may reduce fibrin degradation, maintain integrity and stability. In an aspect, the autologous fibrin scaffold may further include an antifibrinolytic agent. Use of an antifibrinolytic agent may not affect cell viability. In an aspect, the antifibrinolytic agent may be, but is not limited to tranexamic acid, aminocaproic acid (ε-aminocaproic acid), aprotinin, or a lysine-like drug that interferes with the formation of the fibrinolytic enzyme plasmin. In one aspect, the antifibrinolytic agent may be tranexamic acid.

The autologous fibrin scaffold may further include patient-derived culture compounds extracted from the patient's bone marrow. Non-limiting examples of patient-derived culture compounds include fibronectin, at least one growth factor, platelets, at least one cytokine, at least one enzyme, and combinations thereof. The at least one growth factor may include, but is not limited to erythropoietin (EPO), Darbapoietin, G-CSF (granulocyte colony-stimulating factors), or GM-CSF (granulocyte macrophage colony-stimulating factors). Non-limiting examples of the at least one cytokine include SCF, GM-CSF, G-CSF, TGF-beta, IL-6, IL-7, IL-8, and IL-11. The at least one enzyme may include, but is not limited to lactic dehydrogenase (LDH), glutamic-oxalacetic transaminase (GOT), and acid and alkaline phosphatase.

The cells associated with a hematological or metastatic malignancy may include, but are not limited to, acute lymphoblastic leukemia cells, acute myelogenous leukemia cells, chronic lymphocytic leukemia cells, acute monocytic leukemia cells, Hodgkin's lymphoma cells, non-Hodgkin's lymphoma cells, multiple myeloma cells, metastatic cells, and solid tumor cells. In one aspect, the cells associated with a hematological or metastatic malignancy may be multiple myeloma cells. The multiple myeloma cells may be de-differentiated.

The method may further include administering a dose of a drug to the tissue-engineered bone marrow. In an aspect, the drug may be a chemotherapeutic drug. Non-limiting examples of drugs include melphalan, bortezomib, carfilzomib, carmustine, cyclophosphamide, doxorubicin hydrochloride liposome, lenalidomide, pamidronate disodium, panobinostat, plerixafor, pomalidomide, prednisone, thalidomide, zoledronic acid, and any drug being tested for treatment of multiple myeloma. In an aspect, the autologous fibrin scaffold may further include a gradient of oxygen and the drug. In this aspect, the autologous fibrin scaffold may mimic the BM niche. The concentration of oxygen may decrease as a function of depth in the autologous fibrin scaffold. Furthermore, hypoxia in the patient-derived cells cultured on the autologous scaffold may increase as a function of depth in the autologous fibrin scaffold.

The effectiveness of the drug and the dose may be determined by drug uptake by the plurality of cells or cell death of the multiple myeloma cells. Predicting the drug response in the patient may include determining patient specific drug resistance. Non-limiting examples of diseases the patient may have include hematologic malignancies, multiple myeloma, and bone metastasis of solid tumors.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

EXAMPLES

The following examples illustrate the invention.

Example 1

Cells for the 3DTEBM

The MM cell line (MM1s, and MM1s-GFP-Luc) and BM stromal cell (BMSC) line Hs5 were a kind gift from Dr. Irene Ghobrial, Dana-Farber Cancer Institute, Harvard Medical School, Boston, Mass. Human umbilical vein endothelial cells (HUVECs) were purchased from Lonza. All cells were cultured at 37° C., 5% $CO_2$; MM1s cells in RPMI1460 media (Corning CellGro, Mediatech, Manassas, Va.) supplemented with 10% fetal bovine serum (FBS, Gibco, Life technologies, Grand island, N.Y.), 2 mmol/L of L-glutamine, 100 U/mL Penicillin and 100 μg/mL Streptomycin (CellGro, Mediatech, Manassas, Va.), HUVECs in EGM-2 completed media (Lonza, Walkersville, Md.), and stromal cells (Hs5) in Dulbecco's Modified Eagle's Medium (DMEM, Corning CellGro, Mediatech, Manassas, Va.) supplemented with 20% FBS, L-glutamine, and penicillin and streptomycin. Before experiments MM1s, Hs5 stromal cells, and HUVECs (1×106 cells/ml) were pre-labeled with calcein violet (1 μg/mL), DiD (10 μg/mL), or DiI (10 μg/mL) for 1 hour, respectively. In CD markers expression studies, MM1s were prelabed with DiD (10 μg/mL).

Primary $CD138^+$ and $CD138^-$ cells were isolated from bone marrow (BM) aspirates of MM patients from the Siteman Cancer Center, Washington University in Saint Louis. In case of frozen samples, cells were viable frozen at −80° C. in FBS with 10% Dimethyl sulfoxide (DMSO). Plasma samples were extracted from bone marrow aspirates by centrifugation at 1620 g for 10 min, and finally frozen at −80° C. Informed consent was obtained from all patients with an approval from the Washington University Medical School IRB committee and in accord with the Declaration of Helsinki. Primary CD138+ cells were cultured in RPMI1460 media supplemented with 10% FBS, L-glutamine, penicillin and streptomycin, and primary CD138− in DMEM supplemented with 20% FBS, L-glutamine, penicillin and streptomycin. Before experiments CD138+ and CD138− stromal cells ($1\times10^6$ cells/ml) were pre-labeled with DiO (10 µg/mL) or DiD (10 µg/mL) for 1 hour, respectively.

Experiments were performed in quintuplicates and repeated at least three times. Results were analyzed using student t-test for statistical significance and were considered significantly different for P value less than 0.05.

Example 2

Three-Dimensional (3D) Tissue-Engineered Bone Marrow (3DTEBM) Cultures

The three-dimensional (3D) tissue-engineered bone marrow was formed through cross-linking of fibrinogen (naturally found in the plasma of the BM supernatant) with calcium chloride concentrations 0-4 mg/ml. Gelification time was measured and the calcium chloride concentration that induced the fastest gelification time was selected for further studies. Prevention of degradation of the fibrin fibers and stabilization of the scaffolds were achieved by addition of tranexamic acid 0-10 mg/ml. Stability of the scaffold was measured at 3 weeks by weight of scaffolds compared to the weight of non-stabilized scaffolds, and the tranexamic acid concentration that induced the maximal stabilization was selected for further studies. Briefly, 3DTEBM was formed by mixing the following components to achieve final concentrations of 400 µl/ml plasma, 1 mg/ml calcium chloride, and 4 mg/ml tranexamic acid diluted in RPMI completed media to form 100 µl scaffolds. Scaffolds were allowed to gel for 2 h in 96-well plate in incubator at 37° C., 5% $CO_2$, before being covered with RPMI completed media. The medium was changed at 2- or 3-day intervals during the culture period. Cells were added to the mixing solution before fibrin clotting agents (calcium chloride and tranexamic acid). Morphology of the physico-chemical properties of non-stabilized versus stabilized 3DTEBM was analyzed under microscope (Axiovert 35, Zeiss). Then, MM1s cells were introduced into the scaffold and the structure of 3DTEBM was studied using SEM. Dispersion of MM1s cells-GFP, HUVECs-DiI, and CD138− stromal cells-DiD through the 3DTEBM was tested using fluorescence microcopy (Axiovert 35, Zeiss).

Example 3

Flow Cytometry and Cell Proliferation

For flow cytometry analysis, an internal control (MM1s-calcein violet) was added and a minimum of 5,000 events were acquired using BD FACS Aria (BD Biosciences) and DiVa v6.1.2 software. The data was analyzed using FlowJo program v10 (Ashland, Oreg.). MM cells or CD138+ cells were identified by gating cells with a high GFP/DiO signal (excitement, 488 nm; filter, 530/30 nm); Hs5 stroma or CD138-stromal cells were identified by gating cells with a high DiD signal (excitement, 638 nm; filter, 660/20 nm); HUVECs were identified by gating cells with a high DiI signal (excitement, 488 nm; filter, 585/15 nm); and MM1s cells control were identified by gating cells with a high UV signal (excitement, 355 nm; filter, 450/50 nm). A 3DTEBM was digested with type I collagenase at 25 mg/ml for 2 h at 37° C. Classic bi-dimensional (2D) cultures were washed with PBS and removed by pipetting. The effect of cell density ($5\times10^3$-$50\times10^3$ cells/well) of MM1s-GFP, Hs5 stroma-DiD, CD138− stromal cells-DiD, and HUVECs-DiI on growth rate in mono-cultures at day 3 inside 3DTEBM was measured by flow cytometry. The effect of BM interactions on the growth of MM cells ($30\times10^3$ cells/well); cellular interactions with Hs5 stroma-DiD, CD138− stromal cells-DiD, and HUVECs-DiI ($0\times10^3$-$30\times10^3$ cells/well), or interactions with extracellular matrix (ECM) components such as fibronectin (0-250 ng/ml), were tested at day 3 by flow cytometry.

The optimized parameters from previous studies were further used in 3DTEBM. Cell proliferation in mono-cultures [MM1s-GFP ($30\times10^3$ cells/well), CD138− stromal cells-DiD ($10\times10^3$ cells/well), or HUVECs-DiD ($10\times10^3$ cells/well)] and multi-cultures [MM1s-GFP ($30\times10^3$ cells/well), CD138− stromal cells-DiD ($10\times10^3$ cells/well), HUVECs-DiD ($10\times10^3$ cells/well), and fibronectin (100 ng/ml)] was tested at day 3 in classic 2D cultures and 3DTEBM by flow cytometry.

MM cell proliferation of fresh and frozen primary CD138+ from MM patients was analyzed in monocultures and multi-cultures conditions (addition of CD138− cells and fibronectin) at days 3-7-14 in 3DTEBM versus classic 2D cultures by flow cytometry.

Example 4

Hypoxia Analysis

Hypoxia levels of MM1s-GFP cells ($30\times10^3$ cells/well) in 3DTEBM of different depth of tissue (10-75 µl) and classic 2D cultures were determined using MACSQuant Analyzer (Miltenyi Biotec) and MACSQuantify v2.5 software. The data was analyzed using FlowJo program v10 (Ashland, Oreg.). After 48 h of 3DTEBM or 2D cultures, media was carefully removed and 100 µl of PIM solution (100 µg/ml, Hypoxyprobe, Burlington, Mass.) was added to each well, and incubate at 37° C. for 24 h. Then, 3DTEBM was digested with type I collagenase at 25 mg/ml for 2 h at 37° C., and in 2D cultures PIM solution was removed by fresh media, until samples were washed with PBS and removed by pipetting 2 h later. MM cells were fixed and permeabilized with 4% formalin and 90% cold methanol in PBS, washed with cold PBS, and blocked with 3% FBS in PBS. Cells were stained with allophycocyanin-conjugated anti-PIM (Hypoxyprobe; excitement, 635 nm; filter, 655-730 nm). MM cells were identified by gating cells with a high GFP signal (excitement, 488 nm; filter, 530/30 nm); then MFI of PIM was detected.

Example 5

Flow Cytometry and Drug Survival

Drug uptake of doxorubicin (0-10 µg/ml) by MM1s-GFP cells ($30\times10^3$ cells/well) in 3DTEBM and classic 2D cultures was determined using MACSQuant Analyzer (Miltenyi Biotec) and MACSQuantify v2.5 software. The data was analyzed using FlowJo program v10 (Ashland, Oreg.). MM cells or CD138+ cells were identified by gating cells with a high GFP/DiO signal (excitement, 488 nm; filter, 525/50 nm); Hs5 stroma or CD138− stromal cells were identified by gating cells with a high DiD signal (excitement, 635 nm; filter, 655-730 nm); HUVECs were identified by gating cells with a high DiI signal (excitement, 488 nm; filter, 585/40 nm); and MM1s cells control were identified by gating cells with a high UV signal (excitement, 405 nm; filter, 450/50 nm). After 24 h of 3DTEBM or 2D cultures, media was carefully removed and 100 μl of doxorubicin solution was added to each well, and incubate at 37° C. for 4 h. Then, 3DTEBM was digested with type I collagenase at 25 mg/ml for 2 h at 37° C., and in 2D cultures drug solution was removed by fresh media, until samples were washed with PBS and removed by pipetting 2 h later. In addition, drug uptake of doxorubicin (7.5 μg/ml) by MM1s-GFP cells ($30 \times 10^3$ cells/well) in 3DTEBM of different depth of tissue (25-150 μl) after 4 h treatment was measured by flow cytometry, as previously described.

MM1s-GFP cells ($30 \times 10^3$ cells/well) were cultured in mono-culture or multi-culture conditions [CD138⁻ stromal cells-DiD ($10 \times 10^3$ cells/well), HUVECs-DiD ($10 \times 10^3$ cells/well), and fibronectin 100 ng/ml)] in 3DTEBM and classic 2D cultures. After 2 h gelification of 3DTEBM or adhesion in 2D cultures (cells were culture in 50 μl), 50 ul of RPMI completed media was added on top of 3DTEBM. Then, 50 μl of bortezomib (0-30 nM), carfilzomib (0, 10 nM), or melphalan (0, 1 μM) solutions were added on top of 2D cultures and 3DTEBM for 24 h. Cell proliferation assay was assessed by flow cytometry as previously described. Briefly, drug-media was removed, 3DTEBM were digested and cells of 2D cultures detached by pipetting. Effect of drug treatment in MM1s-GFP cells was measured and normalized to non-treated conditions.

Example 6

CD Markers Expression Using Flow Cytometry

The effect of 3DTEBM and classic 2D cultures on CD markers expression was tested at day 3 by MACSQuant Analyzer (Miltenyi Biotec) and MACSQuantify v2.5 software. The data was analyzed using FlowJo program v10 (Ashland, Oreg.). MM1s-DiD cells ($30 \times 10^3$ cells/well) were cultured in mono-culture or multi-culture conditions [CD138⁻ stromal cells ($10 \times 10^3$ cells/well), HUVECs ($10 \times 10^3$ cells/well), and fibronectin 100 ng/ml)] in 3DTEBM and classic 2D cultures. After 3 days, 3DTEBM cultures were digested with type I collagenase at 25 mg/ml for 2 h at 37° C. Classic bi-dimensional (2D) cultures were washed with PBS and removed by pipetting. Then, MM cells were washed with PBS and incubated with each of the following monoclonal antibodies: mouse anti-human CD19, CD22 and CD38– fluorescein isothiocyanate (FITC; excitement, 488 nm; filter, 525/50 nm), CD20 and CD138– phycoerythrin (PE; excitement, 488 nm; filter, 585/40 nm), CD56–V450 (excitement, 405 nm; filter, 450/50 nm), and CD34–PeCy7 (tandem fluorochrome that combines PE and a cyanine dye; excitement, 488 nm; filter, 750 nm LP) on ice for 1 hour. MM cells were identified by gating cells with a high DiD signal (excitement, 635 nm; filter, 655-730 nm), and then MFI of the previous CD markers was detected.

Example 7

Effect of Physico-Chemical Properties in 3DTEBM

The preparation of 3DTEBM was through cross-linking of fibrinogen by calcium ions and addition of antifibrinolytic agent to stabilize the scaffold. The gelification time of 3DTEBM as a function of the calcium chloride ($CaCl_2$) concentration was analyzed. $CaCl_2$ concentration of 1 mg/ml induced the fastest gelification time around 10 min (FIG. 1A). Stability of 3DTEBM as a function of the tranexamic acid concentration was measured. Tranexamic acid concentration of 4 mg/ml induced maximal stabilization of the scaffold, and higher concentrations of tranexamic acid did not increase the stability of 3DTEBM (FIG. 1B). FIG. 1C shows visual images of the 3DTEBM before and after cross-linking and stabilization with optimized conditions (1 mg/ml $CaCl_2$ and 4 mg/ml tranexamic acid). FIG. 1D represents the conceptual design of cell culture inside the optimized 3DTEBM.

Example 8

Cell Growth Inside 3DTEBM

Figure 2C:
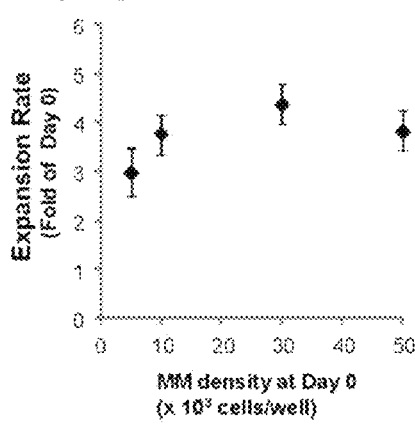
FIG. 2C shows the effect of MM cell density ($5 \times 10^3$-$50 \times 10^3$ cells/well) in MM proliferation inside 3DTEBM at day 3.
Figure 2D:
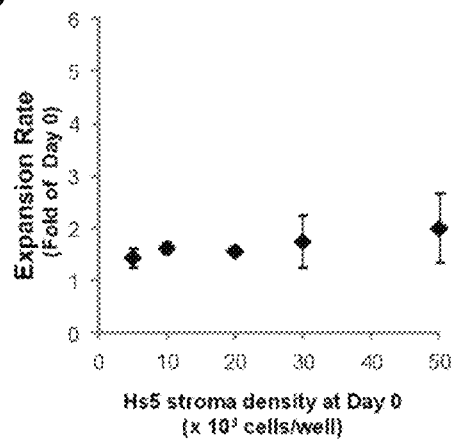
FIG. 2D shows the effect of stroma cell density ($5 \times 10^3$-$50 \times 10^3$ cells/well) in Hs5 stroma proliferation inside 3DTEBM at day 3.
Figure 2E:
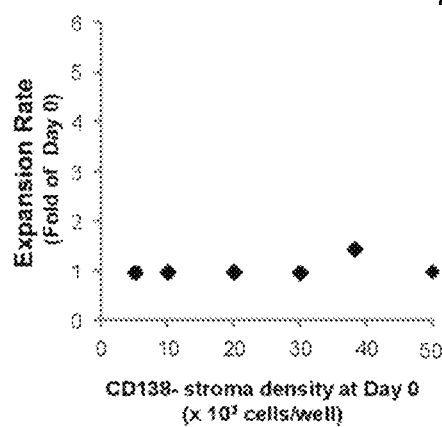
FIG. 2E shows the effect of stroma cell density ($5 \times 10^3$-$50 \times 10^3$ cells/well) in CD138$^-$ stroma proliferation inside 3DTEBM at day 3.
Figure 2F:
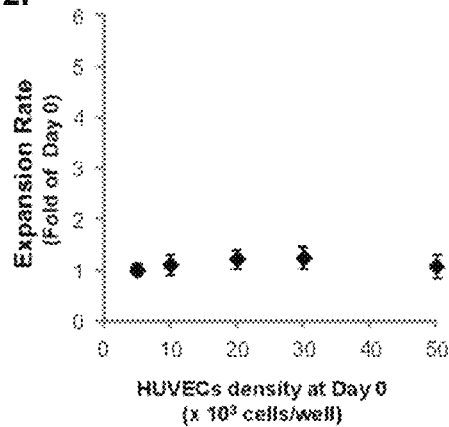
FIG. 2F shows the effect of endothelial cell density ($5 \times 10^3$-$50 \times 10^3$ cells/well) in HUVECs proliferation inside 3DTEBM at day 3.

SEM images revealed that 3DTEBM had a porous structure with a network of interconnected fibers (FIG. 2Ai). MM cells were able to interact with the fibers of the 3DTEBM after 3 days in cell culture (FIG. 2Aii). Fluorescence microscopy images showed that MM1s (FIG. 2Bi), HUVECs (FIG. 2Bii), and CD138⁻ stroma cells (FIG. 2Biii) were able to interact in the 3DTEBM with homogenous growth of the three cell types through the 3DTEBM after 3 days in culture. Moreover, the effect of cell density of each cell type (MM1s, Hs5 stroma, CD138– stroma, and HUVECs) on their own growth rate when cultured alone in 3DTEBM was found to be mainly relevant for MM1s cells. The optimal density for MM cell growth was found at a density of 30,000 cells per well in which it produced about 4.5-fold increase in 3 days (FIG. 2C). However, cell density did not have an effect on the growth rate of Hs5 stroma (FIG. 2D), CD138– stroma cells (FIG. 2E), or HUVECs (FIG. 2F).

Example 9

Effect of BM Interactions on the Growth of MM Cells in 3DTEBM

To mimic the interactions in the BM, co-culture of MM cells with accessory cells and ECM components was tested. Hs5 stroma cell line mildly increased (about 20%) the growth of MM cells at all cell densities in the 3DTEBM compared to MM alone at day 3 (FIG. 3A). However, CD138⁻ stroma cells from MM patients increased the growth of MM cells in the 3DTEBM with a positive correlation, the higher the cell density the higher the growth of MM until at a cell density of 20,000-30,000 cells per well that MM reaches the top growth with an increase about 250% at day 3 (FIG. 3B). In the same way, HUVECs increased the growth of MM cells in the 3DTEBM until at a cell density of 20,000 cells per well that reaches the top of MM growth with an increase about 250% at day 3 (FIG. 3C). The optimal stromal and endothelial density for further experiments in multi-culture conditions, for MM cell growth in 3DTEBM was defined at a density of 10,000 cells per well of each cell type (HUVECs and CD138⁻ stroma cells) in which it produced about 200% increase each cell type in 3 days. In addition, the ECM component fibronectin increased the growth of MM cells in 3DTEBM by about 25% when added at a concentration of 100 ng/ml at day 3 (FIG. 3D). The optimal fibronectin concentration for all the further experiments in multi-culture conditions was defined as 100 ng/ml for MM cell growth in 3DTEBM.

The effect of mono-culture and multi-culture conditions in the classic 2D tissue culture systems compared to the 3DTEBM in MM, CD138⁻ stroma and HUVECs growth was evaluated. While MM cells doubled within 3 days in mono-culture in classic 2D cultures, the multi-culture induced about 2.2-folds additional growth in 2D compared to day 0. In contrast, in the 3DTEBM mono-culture of MM cells induced about 5-fold increase in 3 days (compared to day 0), and the multi-culture in the 3DTEBM promoted about 10-fold increase of MM1s growth (compared to day 0) (FIG. 3E). However, monoculture or multi-culture conditions in the classic 2D tissue culture systems compared to the 3DTEBM did not have an effect on the growth rate of HUVECs and CD138⁻ stroma cells (FIG. 3E).

Example 10

Sustain Survival of Primary Myeloma Cells Ex-Vivo

Figure 4A:
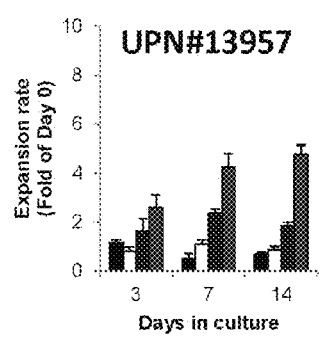
FIG. 4A shows the growth of three primary frozen CD138$^+$ cells in mono-culture or multi-culture conditions in classic 2D cultures or inside 3DTEBM at days 3, 7, and 14 of a newly diagnosed MM patient.
Figure 4B:
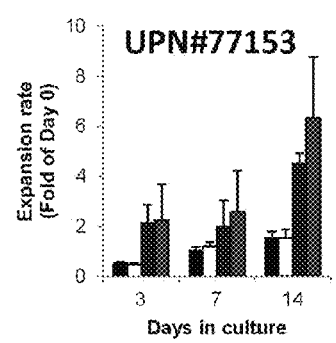
FIG. 4B shows the growth of three primary frozen CD138+ cells in mono-culture or multi-culture conditions in classic 2D cultures or inside 3DTEBM at days 3, 7, and 14 of a newly diagnosed MM patient.
Figure 4C:
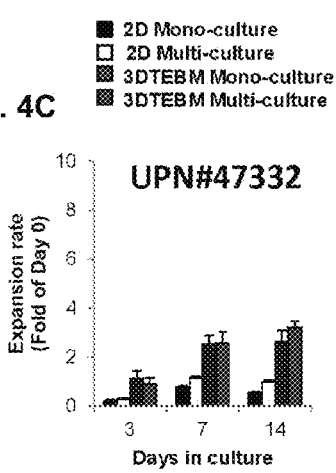
FIG. 4C shows the growth of three primary frozen CD138+ cells in mono-culture or multi-culture conditions in classic 2D cultures or inside 3DTEBM at days 3, 7, and 14 of a progressive/relapse MM patient.

The effect of mono-culture and multi-culture conditions in the classic 2D tissue culture systems compared to the 3DTEBM in fresh and frozen CD138$^+$ primary MM samples was evaluated. Three independent frozen cells from MM patients (newly diagnosed MM patient (FIG. 4A), newly diagnosed MM patient (FIG. 4B), and progressive/relapse MM patient (FIG. 4C)) showed different growth rate in 3DTEBM compared to classic 2D cultures after 14 days. While frozen primary CD138$^+$ cells from MM patients induced less than 2-fold increase within 14 days in mono-culture and multi-culture in classic 2D cultures, the 3DTEBM mono-culture induced about 2 to 4-folds additional growth compared to day 0, and the 3DTEBM multi-culture induced about 3 to 6-fold increase within 14 days (compared to day 0).

Example 11

Effect of 3DTEBM in Hypoxia and Drug Resistance

Figure 5A:
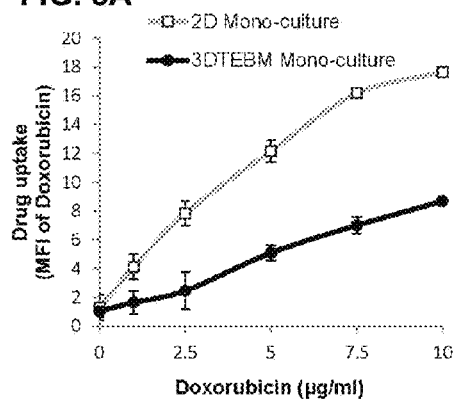
FIG. 5A shows the effect of doxorubicin (0-10 μg/ml) drug uptake in MM cells cultured in 3DTEBM compared to classic 2D cultures after 4 h drug treatment, $p<0.02$.
Figure 5B:
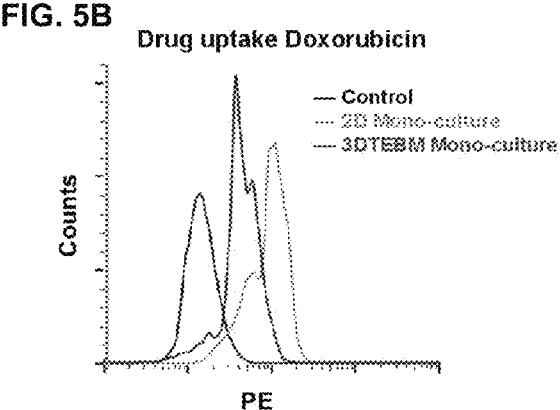
FIG. 5B is a flow cytometry histogram representing the MFI of doxorubicin (Phycoerythrin-PE) in MM cells grown in 3DTEBM vs 2D cultures after 4 h of treatment with 5 μg/ml of doxorubicin. (Control cells are untreated MM cells).
Figure 5C:
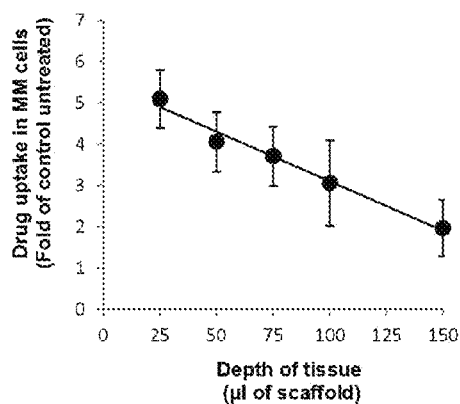
FIG. 5C shows the correlation between depth of tissue (25-150 μl 3DTEBM) and drug uptake by MM cells grown in 3DTEBM after 4 h of treatment with 7.5 μg/ml of doxorubicin.

To test if the 3DTEBM is a three-dimensional structure with a gradient of both oxygen and drug concentration, such as the BM niche, the drug uptake and hypoxic state of MM cells was analyzed as a function of the depth of tissue. After 4 h of treatment with doxorubicin, significantly fewer (p<0.02) MM cells in the 3DTEBM exhibited 2-fold less drug uptake than MM cells grown in classic 2D cultures at all the drug concentrations tested (FIG. 5A). Flow cytometry histogram for 5 µg/ml doxorubicin treatment showed that MM cells grown in 3DTEBM had drug uptake expressed by higher PE fluorescence intensity compared to control MM cells untreated (FIG. 5B). However, MM cells of 3DTEBM compared to 2D cultures had lower PE fluorescence intensity, which means that a part of the MM population in 3DTEBM contained lower concentration of drug that is presented in the cells cultured in 2D. In addition, drug uptake of MM cells grown in 3DTEBM was inversely correlated with the depth of the tissue; with increasing tissue depth the drug uptake by MM cells decreased (FIG. 5C).

Figure 5D:
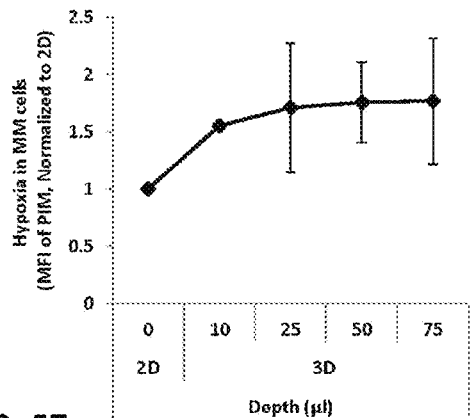
FIG. 5D shows the correlation between depth of tissue (10-75 μl 3DTEBM) and hypoxia by MM cells grown in 3DTEBM compared to hypoxia state of MM cells in 2D cultures.

To test the effect of 3DTEBM in hypoxia, the hypoxic state of the MM cells was analyzed. MM cells in the 3DTEBM exhibited higher hypoxia levels (MFI of PIM) compared to MM cells grown in classic 2D cultures, with increasing tissue depth the hypoxia levels of MM cells showed about 1.75-fold increase at day 3 (FIG. 5D). Deeper scaffolds did not show an increase in hypoxic levels (data not shown), probably due to a mix of hypoxic and normoxic cells from the bottom and top of the scaffold, respectively.

Figure 5E:
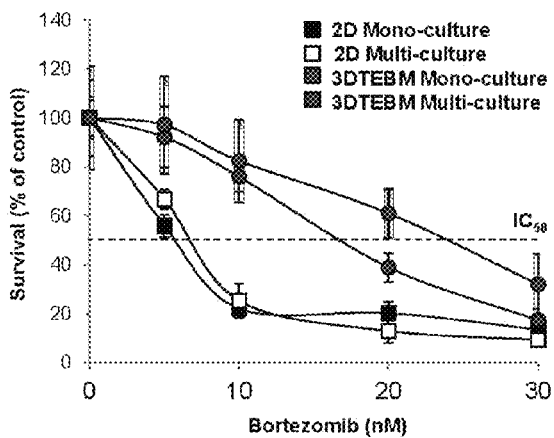
FIG. 5E shows the effect of classic 2D cultures and 3DTEBM, in mono- or multi-culture conditions, on the IC50 of bortezomib in MM1s cells after 24 h.
Figure 5F:
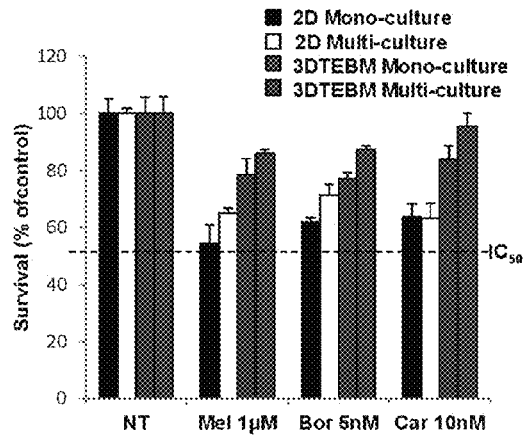
FIG. 5F shows the effect of classic 2D cultures and 3DTEBM, in mono- or multi-culture conditions, on the IC50 of melphalan (1 μM), bortezomib (5 nM), and carfilzomib (10 nM) in MM1s cells after 24 h.

Finally, the effect of increasing concentrations of bortezomib on the survival of MM1s cells grown in mono-culture or multi-culture in 3DTEBM and 2D cultures was measured. The IC50 in 2D mono-culture was as expected around 5 nM and in 2D multi-culture conditions it induced more resistance and the IC50 was around 7 nM. While 3DTEBM mono-culture induced a stronger resistance with IC50 between 15-20 nM, MM cells in the 3DTEBM multi-culture showed the highest resistance with IC50 around 25 nM (FIG. 5E). Accordingly, the same results were found with other drugs, including carfilzomib and melphalan. In classic 2D mono-culture approximately about 40-50% of the MM cells were killed using the different chemotherapies (melphalan 1 µM, bortezomib 5 nM, and carfilzomib 10 nM), the culture of MM cells in 3DTEBM decreased the sensitivity of MM cells to treatment, and addition of multi-culture decreased the sensitivity of MM cells to treatment in both 3D and 2D systems. Multi-culture of MM cells in the 3DTEBM killed only 5-15% of the MM cells for the same drug concentrations (FIG. 5F).

Example 12

3TEBM Induces De-Differentiation of MM Cells

To investigate the effect of 3DTEBM on CD markers expression, we cultured MM cells in mono-culture or multi-culture conditions in 3DTEBM and classic 2D cultures for 3 days. We tested the expression of plasma cell markers including CD38, CD56 and CD138, B cell surface markers including CD19, CD20 and CD22, which are lost upon terminal differentiation into mature plasmocytes, and the hematopoietic stem cell marker CD34. MM cells expressed loss of the plasma cells markers CD38 and CD56, and significant decreased of CD138, in 2D multi-culture and 3DTEBM mono-cultures and multi-cultures compared to 2D mono-culture (FIG. 6A). B cells markers expression such as CD19, CD20, was mildly reduced, with no changes for CD22 in the different culture conditions (FIG. 6B). Moreover, the stem cell marker CD34 was significantly increased in 3DTEBM mono-cultures and multi-cultures compared to 2D mono-culture (FIG. 6C).

What is claimed is:

1. A tissue-engineered bone marrow for personalized therapy of a patient comprising:
   an autologous fibrin scaffold comprising fibrinogen isolated from the patient's bone marrow; and
   a plurality of patient-derived cells isolated from the patient's bone marrow, comprising cells associated with a hematological or metastatic malignancy, wherein the cells associated with a hematological or metastatic malignancy are selected from acute lymphoblastic leukemia cells, acute myelogenous leukemia cells, chronic lymphocytic leukemia cells, acute monocytic leukemia cells, Hodgkin's lymphoma cells, non-Hodgkin's lymphoma cells, multiple myeloma cells, metastatic cells, and solid tumor cells,
   wherein the patient-derived cells are cultured on the autologous fibrin scaffold.

2. The tissue-engineered bone marrow of claim 1, wherein the autologous fibrin scaffold further comprises an antifibrinolytic agent.

3. The tissue-engineered bone marrow of claim 1, wherein the autologous fibrin scaffold further comprises a patient-derived culture compound extracted from the patient's bone marrow, the patient-derived culture compound selected from the group consisting of: fibronectin, at least one growth factor, platelets, at least one cytokine, at least one enzyme, and combinations thereof.

4. The tissue-engineered bone marrow of claim 1, further comprising a drug.

5. The tissue-engineered bone marrow of claim 4, wherein the autologous fibrin scaffold further comprises a gradient of oxygen and a gradient of the drug.

6. The tissue-engineered bone marrow of claim 1, wherein the cells associated with a hematological or metastatic malignancy are multiple myeloma cells.

7. A method of preparing a tissue-engineered bone marrow for personalized therapy of a patient comprising:
   aspirating the patient's bone marrow;
   separating a cellular fraction and a supernatant;
   isolating a plurality of patient-derived cells from the cellular fraction, the patient-derived cells selected from the group consisting of cells associated with a hematological or metastatic malignancy, bone marrow stromal cells, endothelial cells, and combinations thereof;
   creating an autologous fibrin scaffold comprising fibrinogen isolated from the supernatant; and
   culturing the plurality of patient-derived cells on the fibrin scaffold.

8. The method of claim 7, wherein the autologous fibrin scaffold further comprises an antifibrinolytic agent.

9. The method of claim 7, wherein the autologous fibrin scaffold further comprises a patient-derived culture compound isolated from the supernatant, the patient-derived culture compound selected from the group consisting of: fibronectin, at least one growth factor, platelets, at least one cytokine, at least one enzyme, and combinations thereof.

10. The method of claim 7, further comprising administering a dose of a drug to the tissue-engineered bone marrow.

11. The method of claim 10, wherein the autologous fibrin scaffold further comprises a gradient of oxygen and a gradient of the drug.

12. The method of claim 7, wherein the cells associated with a hematological or metastatic malignancy are selected from acute lymphoblastic leukemia cells, acute myelogenous leukemia cells, chronic lymphocytic leukemia cells, acute monocytic leukemia cells, Hodgkin's lymphoma cells, non-Hodgkin's lymphoma cells, multiple myeloma cells, metastatic cells, and solid tumor cells.

* * * * *